United States Patent [19]

Nakatsuka et al.

[11] Patent Number: 4,740,903

[45] Date of Patent: Apr. 26, 1988

[54] DATA PROCESSING SYSTEM FOR CHROMATOGRAPHY

[75] Inventors: Kiyoharu Nakatsuka, Suita; Shinei Ikeou, Minoo, both of Japan

[73] Assignee: Sumitomo Chemical Co., Ltd., Osaka, Japan

[21] Appl. No.: 733,879

[22] Filed: May 14, 1985

[30] Foreign Application Priority Data

May 15, 1984 [JP] Japan ................................. 59-98362

[51] Int. Cl.⁴ ............................................. G06F 15/20
[52] U.S. Cl. ................... 364/497; 73/23.1; 364/571
[58] Field of Search ............... 364/497, 498, 571, 572, 364/526; 204/1 T, 406; 356/432, 436, 441, 442, 325; 73/231, 27 R; 324/71.5

[56] References Cited

U.S. PATENT DOCUMENTS

| | | | |
|---|---|---|---|
| 4,468,742 | 8/1984 | Jenden et al. | 364/497 |
| 4,482,966 | 11/1984 | Mito et al. | 364/497 X |
| 4,524,420 | 6/1985 | Glodo et al. | 364/497 |

Primary Examiner—Gary V. Harkcom
Assistant Examiner—H. R. Herndon
Attorney, Agent, or Firm—Kerkam, Stowell, Kondracki & Clarke

[57] ABSTRACT

A system for processing chromatographic data which comprises an input for data representative of two chromatograms x and y, a memory for storing the inputted data of the chromatograms, and a computer operative to read out, from the memory, retention times $x_i$ and $y_i$ ($i=1, \ldots, n$; $n \geq 2$) of at least two principal peaks of the chromatograms, respectively, and derive one function for converting the retention times $x_i$ to $y_i$ using the chromatogram y as the reference chromatogram, which gives a minimum estimated error. The computer is further operative to calculate, on the basis of the derived function, the modified retention time $x'_j$ of all the peaks of the chromatogram x. Therefore, the system permits to eliminate errors orginated from the judgment of a skilled person and to indentify and quantitatively analyze chromatogram obtained precisely without skill.

7 Claims, 4 Drawing Sheets

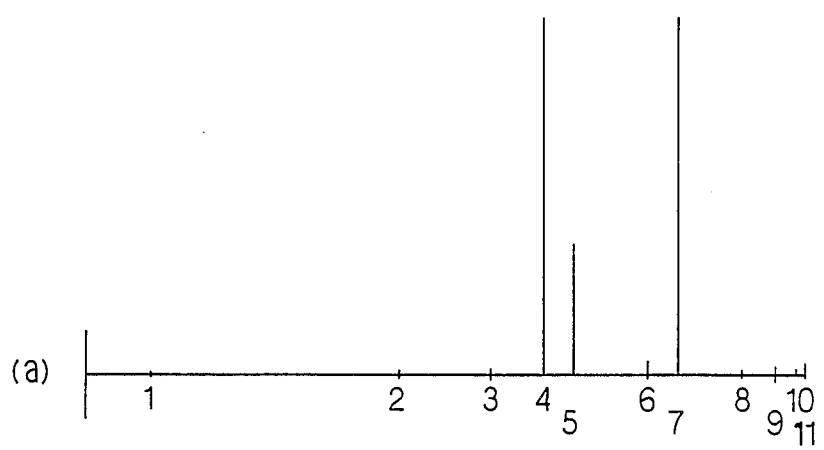
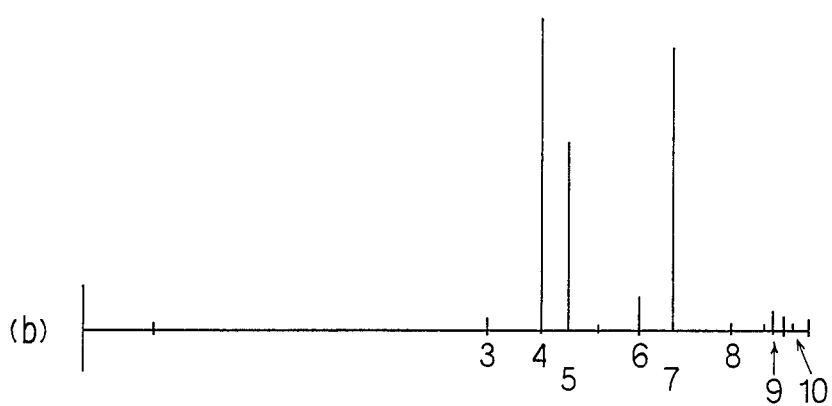
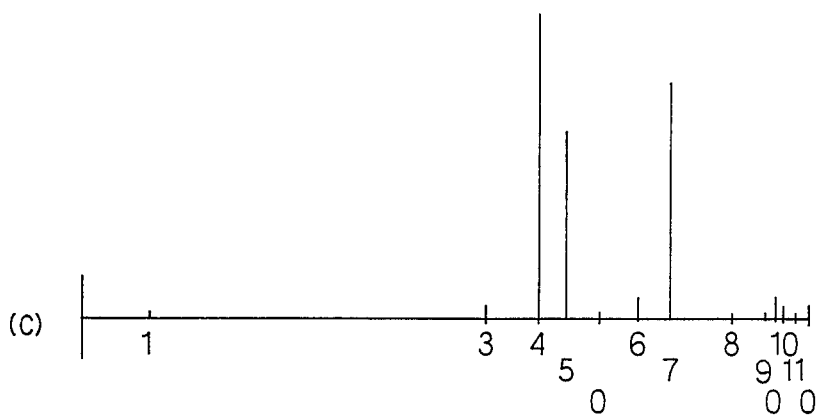

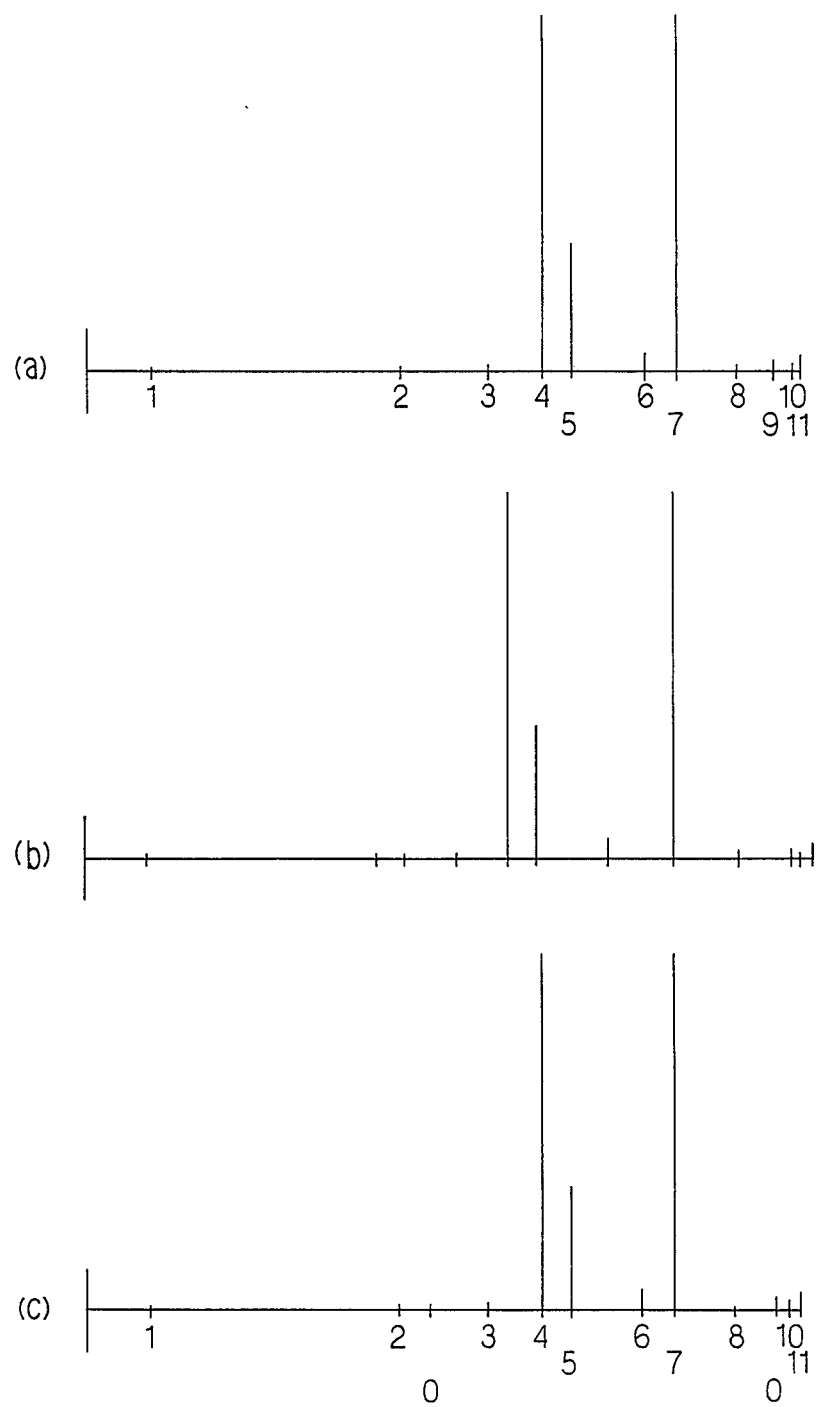

DATA PROCESSING SYSTEM FOR CHROMATOGRAPHY

FIELD OF THE INVENTION

The present invention relates to a data processing system for chromatography and, in particular, to a system for processing chromatograms which are outputted as electric signals by a detector of a chromatography to identify or to quantitatively analyze them without skill.

DESCRIPTION OF THE PRIOR ART

In many fields such as biochemistry, organic chemistry treating natural substances, or the like, it is often needed to isolate each component included in a certain mixture and to qualitatively or quantitatively analyze each component in the form of a compound. However, if such component is thermally instable and complicated in its structure, the means for carrying out such isolation and analysis may remarkably be restricted. Under such circumstances, chromatography technique is believed to be the most excellent and systematized method for isolating and identifying component included in samples to be analyzed, without decomposing or denaturing them.

A typical chromatography technique comprises isolating each component of a sample by passing the sample through a column and detecting the concentration of the components entrained by the moving phase delivered from the column. The detection of the concentration may be performed by observing changes in a physical property of the moving phase, such as refractive index, electric conductivity, dielectric constant, absorbency of light (such as U.V.). In addition, the physical property may be converted by a detector to an electric signal having a magnitude corresponding to the amount of each component and the profile of the signal magnitude is referred to as chromatogram. The electric signal may also be recorded as a chart and may be processed so as to provide the number of peaks, the area, the height and the retention time thereof or the like.

When qualitatively or quantitatively analyzing a sample by the chromatography technique, it is sometimes necessary to compare two or more of chromatograms with each other and to idenify each peak of the chromatograms. Such analysis, in general, comprises calculating area and height of each peak appearing in the chromatogram of each sample obtained according to the chromatography measurement, and then comparing the amount of the principal component or the specific component included in one sample with that of the same component contained in the other sample to identify the peaks.

However, a conventional data processing apparatus for the chromatography simply permits to provide the retention time, the area or the height of each peak for each chromatogram and never provide information on the correspondence between the peaks belonging to different chromatograms and therefore, a skilled person has to judge which peak appearing in each chromatogram corresponds to a specific component of the samples. Thus, such analysis by the chromatography is to examine the correspondence of peaks by comparing a pair of chromatograms (for example, A and B). That is, it is necessary to examine which peak of the chromatogram A corresponds to a specific peak of the chromatogram B and what kind of component is attributed to these peaks. In this case, the component is not necessarily a known one.

The study of such correspondence between the different chromatograms may generally be performed by comparing the retention times of the peaks. However, the retention time is greatly influenced by various factors such as the reproducibility of the chromatography system, the exchange and the aging of the column used and, in particular, a great change in the retention time is observed when the running condition of the system or the sort of the column is changed during the chromatography measurement. Therefore, the examination of the correspondence of the peaks and the analysis of the chromatogram require a great deal of skillfulness. Moreover, even an expert sometimes gives erroneous judgments.

SUMMARY OF THE INVENTION

Taking the aforementioned disadvantages of the conventional chromatography technique into consideration, the inventors of this application have conducted exhaustive studies on the chromatography to develop a new system for processing data obtained according to the chromatography technique, which permits to automatically examine the correspondence between a plurality of chromatograms without the skill and to identify and/or quantitatively analyze peaks.

Then, the main purpose of this invention is to provide a system for processing data (a data processor) obtained according to the chromatographic method.

A further object of the invention is to provide a system which makes it possible to identify and quantitatively analyze the chromatographic data based on the process using regression function, Minimax Method or Spline Function.

A still further object of this invention is to provide a system which permits to automatically examine the correspondence of peaks appearing in different chromatograms.

The aforementioned and other purposes of this invention can be accomplished by using a system (or a data processer) which may be connected to a chromatography system and comprises input means for data representative of two chromatograms x and y, memory means for storing said inputted data of said chromatograms, and computer means operative to read out, from said memory means, retention times $x_i$ and $y_i$ ($i = 1, \ldots, n$; $n \geq 2$) of at least two principal peaks of said chromatograms, respectively, and derive one function for converting said retention times $x_i$ to $y_i$ using said chromatogram y as the reference chromatogram, which gives a minimum estimated error, said computer means being further operative to calculate, on the basis of said derived function, the modified retention time $x'_j$ of all the peaks of the chromatogram x.

BRIEF DESCRIPTION OF THE DRAWINGS

FIGS. 3(a) to (c) and FIGS. 4(a) to (c) show chromatograms obtained in examples 1 and 2 respectively.

DESCRIPTION OF THE PREFERRED EMBODIMENTS

The system of this invention will be explained in more detail, in the light of the embodiments described refering to the attached drawings.

The following explanation will be described using a high performance liquid chromatography system as an example, in order to simplify the explanation, however, the present invention is not restricted to such chromatography at all.

Figure 1:
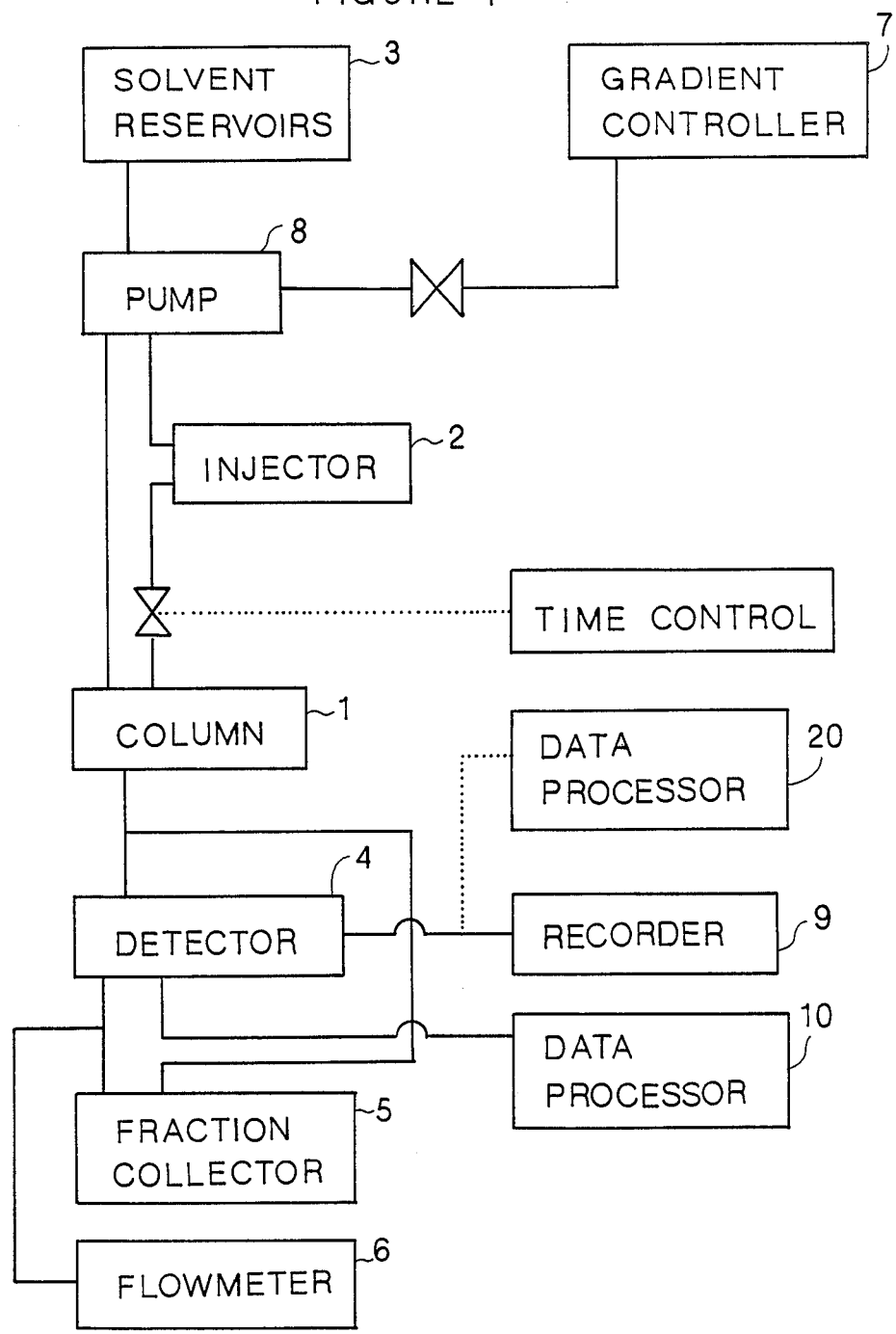
FIG. 1 shows an illustrative block diagram of a typical high performance liquid chromatography system.

In general, a chromatogram may be obtained using a system such as shown in FIG. 1. A sample to be analyzed is firstly injected in a column 1, packed with a certain fixed phase such as silica gel, Zipax (Du Pont), Corasil (Waters Associates), Amberlite (Rohm and Haas), through an injector 2, while introducing an elute (moving phase) from a reservoir 3 into the column 1 continuously. Thus, each component included in the sample is delivered from the bottom of the column in the form of a moving phase which entrains the components in proportion to their retention time, and then passed through a detector 4 and recovered by a fraction collector 5.

The system may optionally be provided with a flowmeter 6 which supplys a signal, in response to the signal outputted from the detector 4, to the fraction collector 5 to control the running condition thereof and thus more complete fractionation of each component by the collector may be permitted.

Moreover, if the elution is carried out according to the gradient elution technique, a device (gradient controller) 7 is connected to a pump 8 and it permits to introduce a plurality of elutes into the column 1 varying the mixing ratio in time.

The detector 4 may be, for instance, UV spectrophotometer, refractometer, fluorescence spectrophotometer, according to the physical property interested and generates electric signals in proportion to the concentration of the component at every instance. The signals are inputted to a recorder 9 or a data processing system 10 wherein the retention time, height, area of each peak are calculated and signals corresponding thereto are inputted to the recorder 9.

As seen from the above discussion, the conventional data processor 10 simply calculates the position (or retention time), the area and/or the height of the peak based on the electric signals outputted by the detector 4, these processed data are recorded by the recorder 9. Therefore, it is not possible to eliminate disadvantages such that the skilled person must judge the correspondence between the peaks, each of which belongs to different chromatograms.

In order to eliminate such disadvantages, the use of a data processing system 20 according to the present invention is quite effective, which may, for instance, be associated to the detector 4 as indicated by the dotted line in FIG. 1.

The system for processing data according to the invention may also be connected to the data processor 10 and, in such embodiment, the processing of the signals inputted to provide a simplified chromatographic chart as shown in FIGS. 3 and 4 in which a bar stands for the area of a peak can be performed by the processor 10. While if the processor of this invention is connected directly to the detector 4, such processing may be performed by the data processing system 20.

Figure 2:
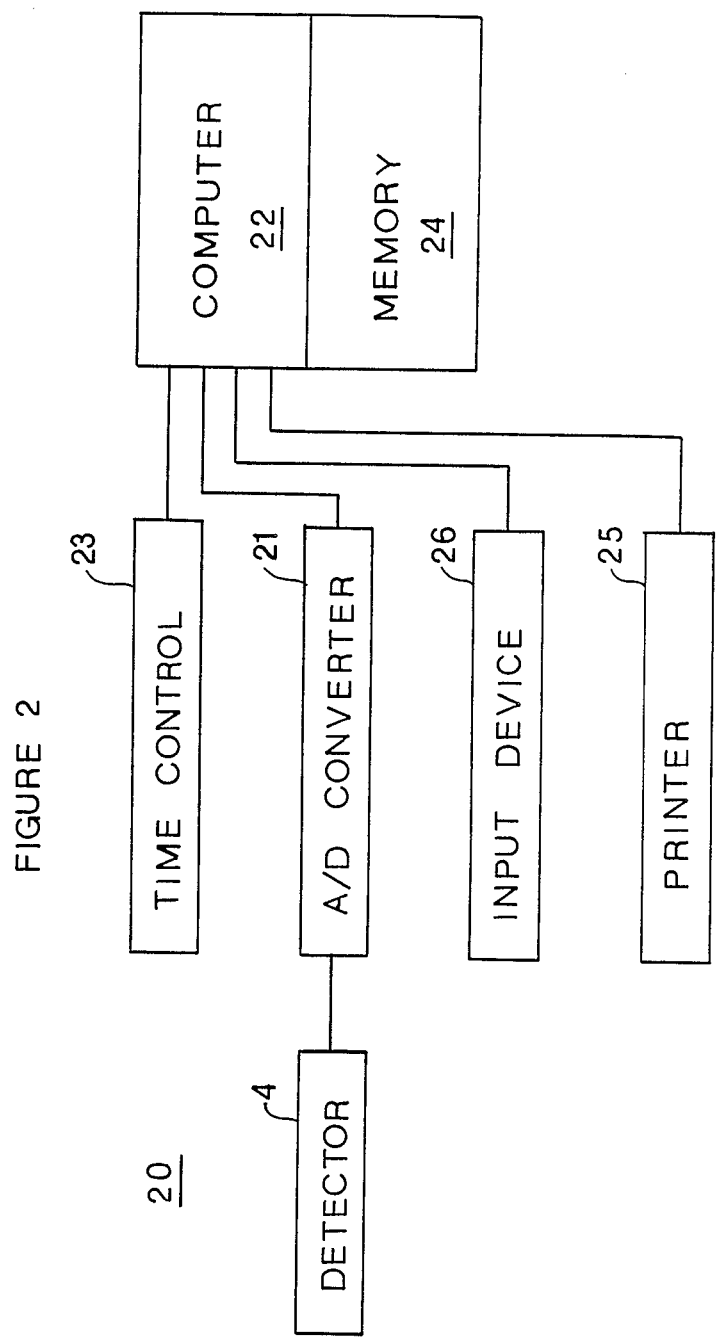
FIG. 2 shows a block diagram of the data processing system for chromatography according to the present invention.

The detailed construction of the data processing system of this invention is shown in FIG. 2. Then, a preferred embodiment thereof is now explained in reference to the attached FIG. 2.

Referring to FIG. 2, there is shown a block diagram illustrating the construction of the data processing system 20 associated to the chromatography system. The data processing system 20 includes an A/D converter 21 having an input connected to the output of the detector 4. This A/D converter 21 is adapted to sample an analog voltage signal at predetermined intervals such as 0.1 second and to convert it to a digital signal consisting of a plurality of bits, which is inputted to a computer 22. This computer 22 also receives a time signal from the time controller 23 which is connected, for example, to the injector 2 at its downstream side. Thus, as is well-known in the art, the computer 22 processes the detected signal inputted thereto so as to determine peaks of the inputted signals, to calculate the area of respective peaks found and to determine the retention time of these respective peaks with reference to the time signal. This data is stored in a memory 24 associated to the computer 22, while the chromatographic data has continuously been measured for each of the given samples, the data being outputted to a printer 25 so that there is printed out a chromatogram in the form of a bar graph as shown in FIGS. 3 and 4.

The aforementioned processing of the detected signals is ordinarily performed in conventional automatic chromatography systems associated with a computer.

In this data processing system, the retention time and the area of all the detected peaks are stored for each sample in the memory 24. After all the chromatography measurement on the samples have been completed, an operator examines all the printed chromatograms and voluntarily selects one chromatogram as the reference one. Furthermore, he determines one or more of the principal peaks in each chromatogram, as the reference times for retention time adjustment. These are inputted through an input device 26 to the computer 22, and then, instructions are also inputted through the input device 26 to the computer 22 for further data processing as mentioned below. Namely, there is read out, from the memory 24, the retention times $y_i$ of the predetermined principal peaks n of the reference chromatogram A and the retention times $x_i$ of the corresponding predetermined principal peaks of a certain chromatogram B selected from the remaining stored chromatogram. For these $y_i$ and $x_i$, the computer 22 performs arithmetic operation, for example, as indicated by the following equations (2) and (3) to determine the coefficients a and b and the term S. Furthermore, the computer 22 calculates, on the basis of the equation (4), modified retention times $x'_j$ of all the remaining peaks appearing in the selected chromatogram B.

The data obtained by the chromatographic method such as shown in FIGS. 3 and 4 may be processed by the computer 22 which processes the data according to any one of a suitable method mentioned below:

(i) Using a certain chromatogram as the reference, the calculation according to a linear regression function is performed in order to convert the retention time(s) of the principal peak(s) of each chromatogram to those of the reference chromatogram.

The method (i) is generally applicable to the case in which there are a plurality of principal peaks in the chromatogram to be processed. For example, if a chromatogram (I) is compared to another chromatogram (II), n principal peaks are selected among the peaks of the chromatogram (I) and each retention time thereof is referred to as $y_i$ ($i=1,2,\ldots,n$) respectively, while the retention time of each corresponding principal peak of the chromatogram (II) is referred to as $x_i$ ($i=1,2,\ldots,n$) and then, the linear regression function may be expressed as follows:

$$y_i = a\,x_i + b + \xi_i \quad (1)$$

$(i = 1,2,\ldots,n)$ wherein $\epsilon_i$ means the estimated error with respect to the peak i and $$\sum_{i=1}^{n} \xi_i^2$$

must be selected so as to be minimum.

The coefficients a and b can respectively be calculated using the following equations:

$$a = \left( n \cdot \sum_{i=1}^{n} y_i \cdot x_i - \sum_{i=1}^{n} y_i \cdot \sum_{i=1}^{n} x_i \right)/S \quad (2)$$

$$b = \left( \sum_{i=1}^{n} x_i^2 \cdot \sum_{i=1}^{n} y_i - \sum_{i=1}^{n} x_i \cdot \sum_{i=1}^{n} y_i \cdot x_i \right)/S \quad (3)$$

$$\text{wherein } S = n \cdot \sum_{i=1}^{n} x_i^2 - \left(\sum_{i=1}^{n} x_i\right)^2.$$

According to the linear regression function thus obtained, all of the peaks appearing in the chromatogram (II) can be converted to $x'_j$ using the coefficients a and b:

$$x'_j = a\,x_j + b \quad (4)$$

The modified retention time ($x'_j$) of the chromatogram (II) thus obtained will substantially consist with that of the corresponding peak ($y_j$) appearing in the chromatogram (I).

In place of the regression function, the function derived by Minimax Method or Spline Function may also be used to convert the retention time of a measured chromatogram to that of the reference chromatogram. However, the regression function is preferably used because of the simplicity of the calculation.

When using Minimax Method, the correspondence of the peaks may be estimated as follows: In the case where the group of retention times ($y_i$, $x_i$) of the selected principal peaks is expressed as a function $y=f(x)$ being continuous within a certain interval of $\alpha \leq x_i \leq \beta$ in the X-Y plane, the function f(x) may be approximated, for instance, by a linear function $p(x)=a_1+a_2x$ wherein the coefficients $a_1$ and $a_2$ are determined so that max $|f(x_i)-p(x_i)|$ becomes minimum for all the values of $x_i\alpha \leq x_i \leq \beta$ ($i=1,2,\ldots,n$). A series of simultaneous equations obtained according to the theory of Haar must be solved to obtain said coefficients.

(ii) Using a polynominal linear regression function with respect to the retention time, the conversion similar to that of the method (i) is performed.

According to the method (ii), the polynomial linear regression function may, for example, be expressed as follows:

$$y = a_0 + a_1 x + a_2 z$$

wherein x and z are respectively independent variables which belong to separate intervals of the chromatogram mentioned below and the coefficients $a_0$ to $a_2$ may be determined so as to minimize the sum of square estimated errors ($U = \Sigma(y_i - a_0 - a_1 x_i - a_2 z_i)^2$; $i=1,\ldots,n$) and practically obtained by solving the following simultaneous equations:

$$\partial U/\partial a_0 = \partial U/\partial a_1 = \partial U/\partial a_2 = 0$$

Thus, a desired polynomial linear regression function is obtained and any other retention time ($x'_j$) may be estimated according to the following equation:

$$x'_j = a_0 + a_1 x_j + a_2 Z_j$$

For example, the data processor 20 derives, on the basis of retention time $x_i$ and $y_i$ ($i=1,\ldots,n$; $n \geq 3$) of at least three principal peaks of the chromatograms x and y, respectively, an piecewise polynomial linear regression function capable of converting $x_i$ to $y_i$, using the chromatogram y as the reference chromatogram, which gives a minimum estimated error in interval defined by each pair of adjacent retention times $x_k$ and $x_{k+1}$ ($k=1$ to $n-1$). The data processor is further operative to convert respective retention time $x_j$ of peaks in the respective intervals $x_k - x_{k+1}$ of the chromatogram x to modified retention times $x'_j$ by the linear regression function for the corresponding interval $x_k - x_{k+1}$. The function for each interval $x_k - x_{k+1}$ can be expressed, for example, as follows:

$$x'_j = a x_j + b$$

where $$a = \left( 2 \cdot \sum_{i=k}^{k+1} y_i \cdot x_i - \sum_{i=k}^{k+1} y_i \cdot \sum_{i=k}^{k+1} x_i \right)/S$$

$$b = \left( \sum_{i=k}^{k+1} x_i^2 \cdot \sum_{i=k}^{k+1} y_i - \sum_{i=k}^{k+1} x_i \cdot \sum_{i=k}^{k+1} y_i \cdot x_i \right)/S$$

$$S = 2 \cdot \sum_{i=k}^{k+1} x_i^2 - \left(\sum_{i=k}^{k+1} x_i\right)^2.$$

The above procedure may also be applicable to the approximation by a higher non-linear regression function. The method (ii) may be useful in the case where there are three or more of principal peaks in the chromatogram to be processed. In this case, the Minimax Method, the Spline Function and the nonlinear regression function may be used instead of the polynomial linear regression function. Moreover, this method is particularly effective to compare chromatograms with each other obtained under different running conditions of the chromatography system.

In the aforementioned methods, the conversion of the retention time is, in general, performed by a single equation. However, when comparing the chromatograms differing in conditions Such as the concentration gradient of the elute used and flow rate of the moving phase in the liquid chromatography, the retention time of the chromatogram is divided into a plurality of regions or intervals in the light of the time at which the running conditions of the chromatography system, such as the concentration gradient of the elute or the flow rate thereof, are changed. That is, within each region, the running condition remains unchanged and a pair of neibouring regions differ in the running conditions of the chromatography system from each other. Therefore, it is preferred or necessary to apply different conversion equation to each region. In such cases, the conversion may be performed by selecting knots at the boundary of each neibouring pair of regions and processing the retention time of a peak belonging to a specific region utilizing a single equation, when the Spline Function is used.

Specifically, if the Spline Function is used, at least one of the principal peaks of the chromatogram x may be used as a knot. Otherwise, all the retention times $x_i$ of the principal peaks are used as the knots. Preferably, the Spline Function is a natural cubic Spline Function and, in this case, it may be derived as follows:

When denoting the selected group of retention times (or knots) as $(x_0, y_0), (x_1, y_1), \ldots, (x_n, y_n)$, the natural cubic Spline Function in a narrow interval $[x_{j-1}, x_j]$ may be referred to as $S_j(x)$ and the value of its second differential coefficient at $x=x_j$ can be referred to as $S_j''(x_j)=M_j$. In addition, the distance of said narrow interval is denoted as $h_j=x_j-x_{j-1}$. While, $S_j''(x)$ should be linear in the interval $[x_{j-1}, x_j]$ and therefore, the following relation must be fulfilled:

$$S_j''(x) = \frac{M_{j-1}}{h_j}(x_j - x) + \frac{M_j}{h_j}(x - x_{j-1})$$

Since the conditions: $S_j(x_j)=y_j$ and $S_j(x_{j-1})=y_{j-1}$ are given, the double integral of the aforementioned second differential $S_j''(x)$ can provide the following equation.

$$S_j(x) = y = M_{j-1}\left(\frac{(x_j - x)^3}{6h_j} - \frac{x_j - x}{6}h_j\right) +$$

$$M_j\left(\frac{(x - x_{j-1})^3}{6h_j} - \frac{x - x_{j-1}}{6}h_j\right) +$$

$$\frac{x_j - x}{h_j}y_{j-1} + \frac{x - x_{j-1}}{h_j}y_j$$

The remaining retention times may be calculated according to this equation. The coefficients $M_j$ ($j=1,2,\ldots, n-1$) may be obtained according to the conditions for continuity:

$$S_j(x_i) = S_{j-1}(x_i); \quad S_j'(x_i) = S_{j-1}'(x_i);$$

$$S_j''(x_i) = S_{j-1}''(x_i)$$

that is, $M_j$ may be calculated by solving the following simultaneous equations:

$$\frac{h_j}{6}M_{j-1} + \frac{h_j + h_{j+1}}{3}M_j + \frac{h_{j+1}}{6}M_{j+1} =$$

-continued
$$\frac{y_{j+1} - y_j}{h_{j+1}} - \frac{y_j - y_{j-1}}{h_j} \quad (j = 1, 2, \ldots, n-1)$$

where $M_0 = M_n = 0$.

The principal peaks should be present in both chromatograms to be analyzed according to the system of this invention and generally, it is preferable to select at least two peaks corresponding to the principal components as the principal peaks.

The principal peaks which constitute the reference for processing retention times may be experientially determined and this is sufficient in most of the cases. However, if there is no principal peak and if the amount of each component separated i.e., the area or the height of each peak appearing in the chromatogram substantially varies, it is effective to determine the principal peak(s) according to a statistical method.

When determining the principal peak(s), it may be possible to utilize a part or whole of the chromatogram to be analyzed or other chromatogram separately obtained. Moreover, the internal standard method may also be used. According to the internal standard method, the peak(s) of the standard material may be used as the principal peak(s), which is obtained by adding a certain standard material to all of the samples and carrying out the chromatography measurement. When a single material is used as the standard, it is preferably selected so that the retention time thereof is equal to a half of the total measuring time and that the peak thereof is situated around the middle part of the chromatogram obtained. While, if a plurality of standard materials are used, these materials are prafarably selected to that the peaks thereof are uniformly distributed over the whole region of the chromatogram. In addition, these standard materials may also be selected so that each peak thereof appears before or behind a certain knot, since the conversion of the retention time is possibly complicated in such a case where the gradient elution condition is changed, particularly, in the liquid chromatography. The amount of the standard material should be determined such that the peaks thereof may easily be distinguished from those of components contained in the sample to be analyzed with respect to the retention time, the area or the height of the peak.

Such internal standard method is quite effective in a case where a sample contains a lot of components (i.e., in a multicomponent system) and the determination of the principal peak(s) is quite difficult. Moreover, it is also possible to use the internal standard method, in the case where the principal peak is easily determined, to make the conversion procedure more easier and accurate.

The invention will be described more concretely by referring to the following illustrative examples. In these examples, all the samples used consist of C. I. Reactive Yellow 76 (available from Sumitomo Chemical Co., Ltd.), provided that the conditions of synthesis and the starting materials differ from each other. All the chromatograms are obtained according to the high performance liquid chromatography system in which Li-Chrosorb RP-18 (manufactured and sold by Sumika Analysis Center) is used as the column and the moving phase consists of a mixture of water and methanol. The chromatography measurement was carried out according to the gradient elution method.

In the attached FIGS. 3 and 4, the chromatogram is presented by a simplified bar graph in which the height of a bar represents the area of a corresponding peak. The retention time is shown on the abscissa and the whole scale thereof equals to about 30 minutes. While the area of the peak is shown on the ordinate wherein the area is normalized so that the sum of the area of the peaks becomes 100 and the full scale thereof is equal to 5 in order to make it possible to easily distinguish the quite short peaks with each other. In FIGS. 3 and 4, the figure (a) is the same chromatogram and used as the reference one for comparison, while the figure (b) corresponds to chromatograms obtained in each example and is to be analysed with respect to the correspondence of the peaks of chromatogram of the example with those of the reference one. The figure (c) represents the chromatogram which is printed out after converting the retention time of the peaks appearing on the chromatogram obtained in each example, according to the system for processing data of this invention. In these figures (b) and (c), the same numeral as in the reference (figure (a)) is given to each peak. This means that the peak having the same numeral as in the figure (a) corresponds to that of the figure (a) having the same numeral. The numeral 0 as seen in the figure (c) means the fact that there is no corresponding peak in the figure (a).

EXAMPLE 1

Using two reaction solutions obtained from different starting materials under different synthetic conditions as the sample to be analyzed, the high performance chromatography measurement was carried out by the chromatography system as shown in FIG. 1 and the resulting two chromatograms are shown in FIGS. 3(a) and (b) respectively.

In FIGS. 3(a) and 3(b), it seems that there is not noticeable discrepancy in each retention time corresponding to peak 4, 5 or 7 between the cromatograms (a) and (b). Therefore, the peaks of the chromatogram (b) may be numbered as in the FIG. 3(b) by comparing each peak appearing in the chromatogram (a) with (b). While, no peak corresponding to the peaks 2 and 11 is observed in the chromatogram (b) and further three unknown peaks are observed between the peaks 5 and 6 and the peaks 8 and 9 and behind the peak 10 respectively.

However, since the small difference in the retention time of each peak ascribed 4, 5 or 7 between the chromatograms (a) and (b) was in fact observed, the retention times of the peaks appearing in the chromatogram (b) was converted using the system according to the invention. The data was processed using the linear regression function and peaks 4, 5 and 7 are used as the principal peaks. The results obtained are shown in FIG. 3(c). The retention time of each peak in the chromatogram (a) quite consists with that of the corresponding peak in the chromatogram (c). This fact clearly means that the highly reliable identification of each peak in the chromatogram is possible, if the analysis was performed using the chromatogram (c) converted by the system of this invention.

EXAMPLE 2

In this example, a chromatogram was obtained according to the same chromatography system as in FIG. 1 except for changing sample and conditions for gradient elution. The gradient elution conditions are changed so that the range between peaks 1 and 4 is narrowed, that the range between peaks 5 and 6 remains unchanged and that the range behind the peak 7 is widened. The resulting chromatogram is shown in FIG. 4(b).

In the chromatograms (a) and (b), the retention times substantially differ from each other. The peaks 4, 5 and 7 have a large peak area and can easily be identified. Therefore, these peaks are used as the principal peaks and the conversion of the retention times appearing in the chromatogram (b) is performed or processed according to the data processing system of this invention.

Each principal peak is selected as the knot and the conversion is performed using a cubic natural Spline Function. The results obtained are shown in FIG. 4(c).

As seen from the above, according to the data processing system of this invention, the chromatographic data may be processed easily and precisely, even when the change of retention time is complicated due to the variation in the running conditions of the chromatography system such as the conditions for gradient elution.

What is claimed is:

1. A data processing system used in combination with a chromatography apparatus and adapted to modify one of at least two chromatograms x and y so that these chromatograms x and y can be compared with each other on the same time axis, comprising:

memory means for storing data representative of said at least two chromatograms x and y;

computer means coupled to the memory means;

setting means coupled to the computer means for selecting one of said at least two chromatograms, i.e. y, as a reference chromatogram y and for designating at least two principal peaks $y_p$ (p=1, ... n; n≧2);

said setting means being used to also select another of said at least two chromatograms, i.e. x, as a chromatogram x to be compared with the reference chromatogram y and to designate principal peaks $x_p$ (p=1, ... n; n≧2) of the same number as that of the designated principal peaks $y_p$ of the reference chromatogram y;

the computer means operating to derive, from the retention times $x_i$ and $y_i$ (i=1, ... n; n≧2) of said designated principal peaks $x_p$ and $y_p$ of the two chromatograms x and y, one function for converting the time axis of the retention times $x_i$ to substantially the same time axis as that of the retention times $y_i$ with a minimum estimated error; and said computer means operating to further calculate, on the basis of said derived function, the modified retention times $x'_j$ of all the peaks of the chromatograms x.

2. A data processing system as set forth in claim 1 wherein said computer means is programmed to calculate $$y_i = ax_i + b + \xi_i \ldots (i=1,\ldots n)$$

where $$a = \left( n \cdot \sum_{i=1}^{n} y_i x_i - \sum_{i=1}^{n} y_i \cdot \sum_{i=1}^{n} x_i \right)/S$$

$$b = \left( \sum_{i=1}^{n} x_i^2 \cdot \sum_{i=1}^{n} y - \sum_{i=1}^{n} x_i \cdot \sum_{i=1}^{n} y_i \cdot x_i \right)/S$$

-continued $$S = n \cdot \sum_{i=1}^{n} x_i^2 - \left(\sum_{i=1}^{n} x_i\right)^2$$

then to determine coefficients a and b with $$\sum_{i=1}^{n} \xi_i^2$$

being minimum, and further to obtain said modified retention time $x'_j$ on the basis of a linear regression function: $x'_j = ax_j + b$.

3. A data processing system as set forth in claim 2 wherein:
said setting means is adapted to cause said computer means to read out, from said memory means, retention time $x_i$ and $y_i$ ($i=1, \ldots, n$; $n \geq 3$) of at least three principal peaks of the chromatograms x and y, respectively; and
said computer means is programmed to derive said linear regression function in each interval defined by each pair of adjacent retention times $x_k$ and $x_{k+1}$ ($k=1$ to $n-1$);
said computer means being operative to also convert respective retention time $x_j$ of peaks in the respective intervals $x_k - x_{k+1}$ of said chromatogram x to modified retention times $x'_j$ by the linear regression function for the corresponding interval $x_k - x_{k+1}$.

4. A data processing system as set forth in claim 1 wherein:
said setting means is adapted to cause said computer means to read out, from said memory means, retention time $x_i$ and $y_i$ ($i=1, \ldots, n$; $n \geq 3$) of at least three principal peaks of the chromatograms x and y, respectively; and
said computer means is programmed to derive one function capable of converting the time axis of the retention times $x_i$ to substantially the same time axis as that of the retention times $y_i$ with a minimum estimated error.

5. A data processing system as set forth in claim 4 wherein said computer means is programmed to use, as said function, a Spline Function using, as a knot, at least one of said principal peaks of said chromatogram x.

6. A data processing system as set forth in claim 5 wherein said computer means is programmed to use all the retention times $x_i$ of said principal peaks as the knots.

7. A data processing system as set forth in claim 6 wherein said computer means is programmed to use, as said Spline Function, a natural cubic Spline Function expressed for each interval $[x_{j-1}, x_j]$ as follows:

$$S_j(x) = y = M_{j-1}\left(\frac{(x_j - x)^3}{6h_j} - \frac{x_j - x}{6} h_j\right) +$$

$$M_j \frac{(x - x_{j-1})^3}{6h_j} - \frac{x - x_{j-1}}{6} h_j + \frac{x_j - x}{h_j} y_{j-1} + \frac{x - x_{j-1}}{h_j} y_j$$

wherein $h_j = x_j - x_{j-1}$, and $M_j$ may be calculated according to the following simultaneous equations:

$$\frac{h^j}{6} M_{j-1} + \frac{h^j + h^{j+1}}{3} M_j + \frac{h_{j+1}}{6} M_{j+1} =$$

$$\frac{y_{j+1} - y_j}{h^{j+1}} - \frac{y_j - y_{j-1}}{h^j}$$

($j = 1, 2, \ldots, n - 1$)

where $M^o = M^n = 0$.

* * * * *